United States Patent [19]

Carson

[11] Patent Number: 4,877,485
[45] Date of Patent: Oct. 31, 1989

[54] SHEET INSPECTION STATION WITH PNEUMATIC SHEET GUIDE

[75] Inventor: Keith J. Carson, Kalamazoo, Mich.

[73] Assignee: Process Automation Business, Inc., Columbus, Ohio

[21] Appl. No.: 320,852

[22] Filed: Mar. 6, 1989

Related U.S. Application Data

[63] Continuation of Ser. No. 56,025, Jun. 1, 1987, abandoned.

[51] Int. Cl.⁴ .................. D21F 7/06; G01N 21/01
[52] U.S. Cl. .................... 162/263; 73/37.7; 73/159; 271/195; 356/431
[58] Field of Search ............... 73/159, 37.7; 271/195; 162/255, 263, 198; 356/431, 430, 429

[56] References Cited

U.S. PATENT DOCUMENTS

| | | | |
|---|---|---|---|
| 3,103,850 | 0/1963 | Khoury | 73/159 |
| 3,629,593 | 0/1971 | Van Brimer | 271/74 |
| 3,633,281 | 0/1972 | Vits | 34/1 |
| 4,131,320 | 0/1978 | Volat et al. | 302/2 R |
| 4,319,847 | 0/1982 | Howarth | 356/431 |
| 4,434,649 | 0/1984 | Williams | 73/159 |
| 4,444,531 | 0/1984 | Baker et al. | 406/88 |
| 4,449,398 | 0/1984 | Williams | 73/37.7 |
| 4,528,507 | 0/1985 | Domin et al. | 324/249 |

Primary Examiner—Steve Alvo
Attorney, Agent, or Firm—Richard H. Berneike

[57] ABSTRACT

A sheet inspection station including pneumatic means for guiding the sheet past one or more measurement sensors in non-contacting fashion, thus eliminating measurement error resulting from fiber/dust buildup associated with friction between the sheet and conventional guide rails. Air is directed from components, that extend from a sensor surface, onto the sheet surface.

4 Claims, 4 Drawing Sheets

SHEET INSPECTION STATION WITH PNEUMATIC SHEET GUIDE

This application is a continuation of application Ser. No. 07/056,025, filed June 1, 1987, now abandoned.

BACKGROUND OF THE INVENTION

1. Technical Field

This invention relates to sheet inspection stations used in the manufacture of continuous-sheet materials such as papers, plastics, foils, and the like. More particularly, it relates to the means by which the sheet of material is guided through the inspection station. Yet more particularly, it concerns sheet inspection stations and associated processes employing pneumatic means for guiding the sheet through the inspection station in non-contacting fashion.

2. Description of Background Art

Continuous-manufacturing processes employ measurement and control systems to derive material savings and enhance quality control. In some industries, notably that of papermaking, sheet inspection stations are used to continuously monitor certain physical properties of a material which is being continuously produced in sheet form. These inspection stations employ one or more measurement sensors. Hereinafter, for any given sheet inspection station, these sensors are collectively referred to as a "sensor package". The sensor package is mounted usually through a carriage or sheet-traversing mechanism on a conventional frame. The frame typically houses a drive system that enables movement of the carriage, with the sensor package, back and forth across the sheet of material so that measurement of the relevant physical properties can be made across the entire cross-machine width of the sheet.

The sensors making up the sensor package are technically sophisticated apparatus that typically employ a source of electromagnetic radiation in conjunction with a radiation detection device in order to produce electrical output signals, the magnitudes of which vary according to the degree of interaction of the radiation with one or more constituents of the sheet. These output signals are delivered to a remote signal processing unit such as a digital computer, where they are appropriately processed to produce measurements of the physical properties of interest.

In most cases, performance of the sensors is impaired if the sheet is permitted to flutter or is not kept perfectly flat in the region where the radiation interacts with the sheet. Therefore, some sensors require that in the region, the sheet be maintained against a flat surface of the sensor. Others employ air bearings within the sensor to maintain the sheet in a substantially constant vertical position as it passes through that region, while preventing contact of the sheet with the sensor. See, for example U.S. Pat. Nos. 4,319,847 Howarth and 4,449,398 Williams. To assist in meeting these requirements, and for other reasons such as prevention of sheet breakage, sheet inspection stations of the above description have heretofore incorporated sheet-contacting guide rails which guide the sheet into and out from the sensor package while maintaining slight tension on the sheet. These are typically rounded, metal rails that are located just outside the sensor package housing and are secured thereto. Although these guide rails are of considerable importance, their method of operation creates a problem that is more or less severe, depending on the type of sensor. Specifically, and especially where the sheet is composed of a fibrous material such as paper, contact of the sheet with the guide rails causes gradual removal of fiber or duct from the sheet. Some of this residual material finds its way into the sensor package and is deposited onto the sensors, thereby impairing sensor performance. A past solution to this problem has been to incorporate "air wipes" in the designs of sensors which are susceptible to such performance impairment. These serve to blow away accumulated residual material and mauy also serve the purpose of maintaining substantially constant air temperature in the region where radiation interacts with the sheet. That solution imposes a requirement that each dust-sensitive sensor contain its own air wipe and, insofar as residue from friction between the sheet and the guide rails is concerned, does not address the problem at its source.

This invention provides a sheet inspection station that eliminates measurement error resulting from fiber/dust buildup associated with friction between conventional guide rails and the sheet. In addition, the invention eliminates the need for periodic replacement of guide rails which are worn flat from continuous contact with the sheet.

SUMMARY OF THE INVENTION

The present invention provides sheet inspection stations and associated processes that employ pneumatic means for guiding a sheet of material past a sensor package in non-contacting fashion. The invention thus eliminates measurement error resulting from the buildup of fiber or dust created by continuous contact of the sheet with conventional guide rails.

In its preferred form, the invention directs streams of air onto the sheet at four different machine-direction positions. Two of these positions are upstream from the sensor package and the streams of air directed thereat cooperate to orient the sheet in accordance with a desired path of motion and guide the sheet into a housing in which the sensor package is contained. The remaining two positions are downstream from the sensor package and the streams of air directed thereat cooperate to maintain the desired orientation of the sheet and guide the sheet out from the housing. The sheet is thus guided past the sensor package in non-contacting fashion. In addition, the streams of air collectively cooperate to effect a slight increase in tension of the sheet over a range which includes the sensor package.

DESCRIPTION OF THE PREFERRED EMBODIMENT

Figure 1:
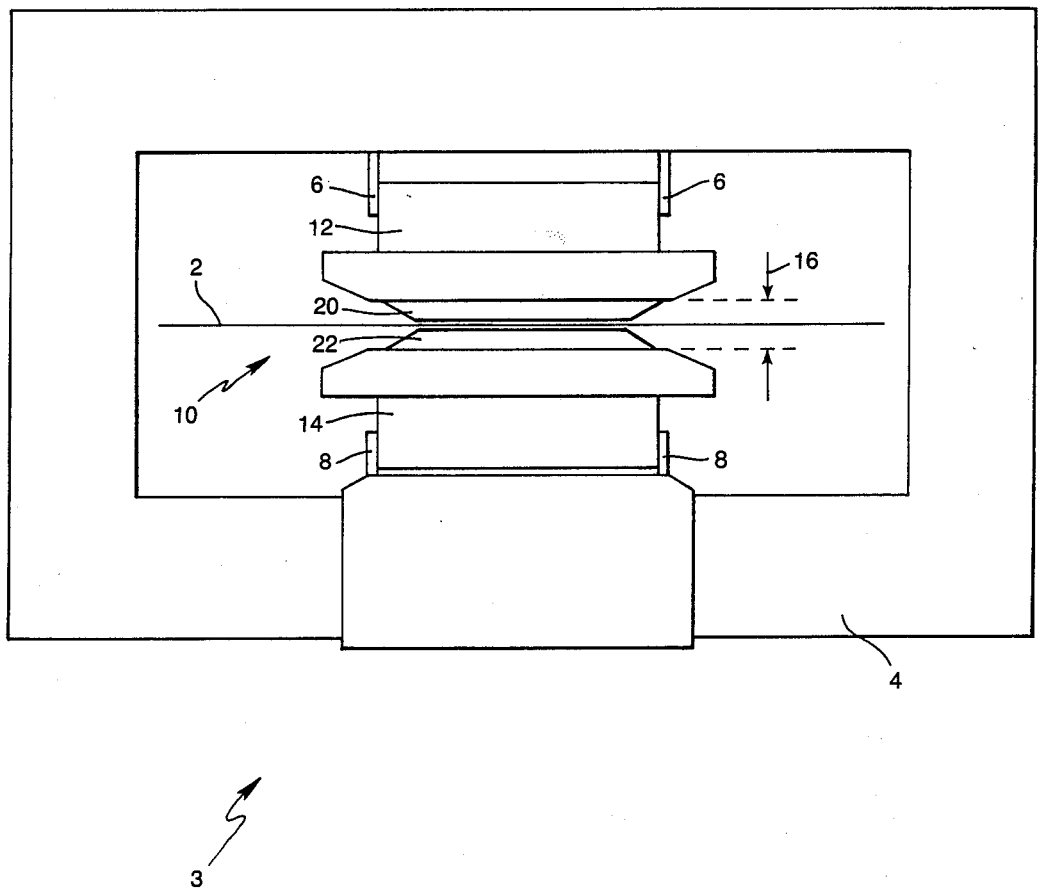
FIG. 1 is a generally schematic representation of an embodiment of the invention.

Referring to FIG. 1, the numeral 2 designates a sheet of material that is in molten during its continuous production. An edge view of the entire cross-machine width of the sheet 2 is indicated. The sheet 2 is illustrated as passing through a sheet inspection station, (designated generally by the numeral 3), and may be viewed as moving into the drawing.

The sheet inspection station 3 includes a conventional frame 4 to which a carriage mechanism comprising an upper carriage member 6 and a lower carriage member 8 is movably secured. The carriage mechanism is mechanically responsive to motion produced by a drive system (not shown) contained in the frame 4. The upper and lower carriage members 6, 8 move together across the sheet 2 to one extreme thereof, and then move back across the sheet to the opposite extreme. This reciprocating motion, hereinafter referred to as "scanning", continues during production of the sheet material, and is effected in a known manner by the drive system.

Figure 3:
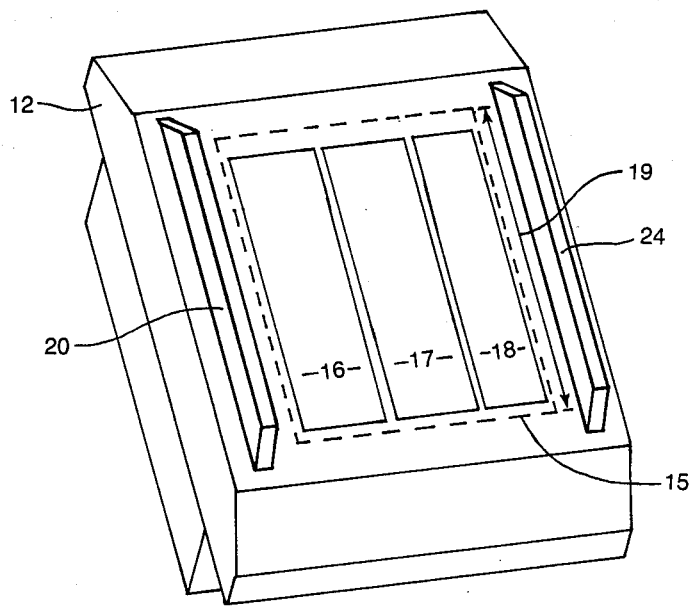
FIG. 3 is a generally perspective but somewhat schematic view illustrating, in accordance with the preferred embodiment of the invention, certain dimensional and positional relationships among the sensor package, the sensor package housing, and the pneumatic means for guiding the sheet.

Housing for a sensor package is indicated generally by the numeral 10 and includes an upper housing 12 rigidly secured to the upper carriage member 6, and a lower housing 14 rigidly secured to the lower carriage member 8. In this embodiment, the desired path of motion for the sheet 2 is through a pass gap 16 separating the upper and lower housings 12, 14. The housing 10 contains a sensor package comprising at least one, but typically plural sensors or gauges adapted to produce electrical signals indicative of one or more physical properties of the sheet 2. These sensors may have both upper and lower portions that are aligned and located in the upper and lower housings 12, 14, respectively, or may have a single portion located in either the upper or lower housing. In FIG. 3, a sensor package is represented by a dashed line 15 enclosing upper portions of three sensors 16, 17, 18. A cross-machine width 19 of the sensor package 15 is defined by the maximum range over which the sensors extend in the cross-machine direction.

Figure 2:
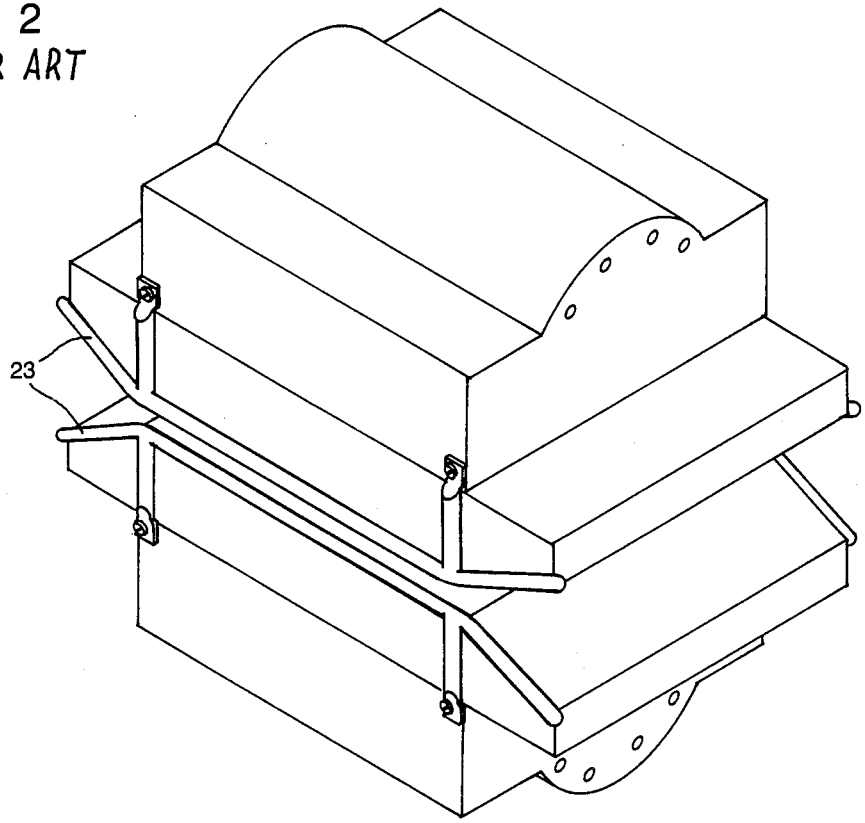
FIG. 2 illustrates a sensor package housing incorporating sheet-contacting guide rails of the prior art.
Figure 5:
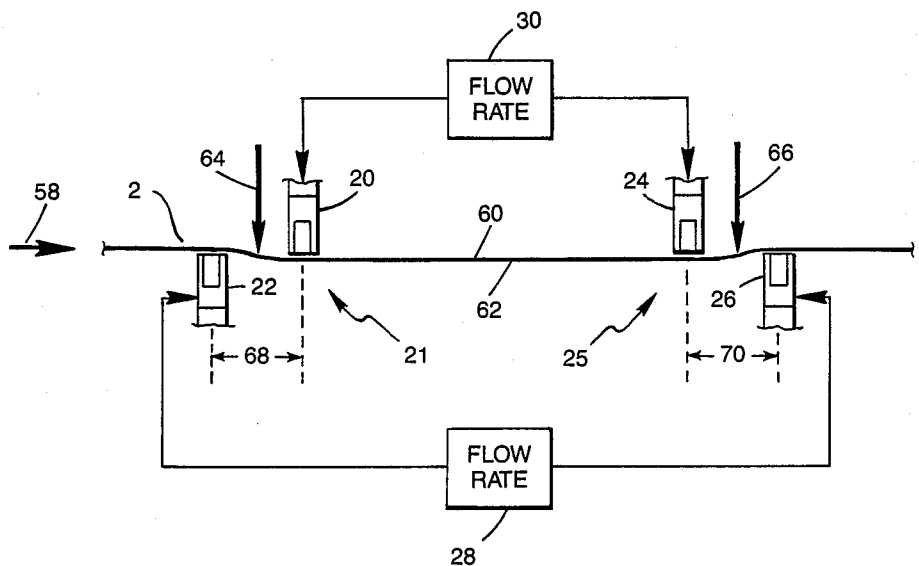
FIG. 5 is a schematic illustration of the method by which the pneumatic means for guiding the sheet operates according to the preferred embodiment.

Referring to FIGS. 1, 3, and 5, pneumatic means for guiding the sheet 2 past the sensor package 15 is provided and includes four air-directing components 20, 22, 24, 26 located between the housing 10 and the sensor package 15. Air is directed from each of these components onto the sheet 2. In contrast with conventional guide rails, (See, e.g. those designated with the numeral 23 in FIG. 2), the air-directing components 20, 22, 24, 26 do not contact the sheet 2 during normal operation.

As best seen for components 20 and 22 in FIG. 1, the components are oriented with respect to the sensor package 15 to direct the sheet 2 through the pass gap 16. As best seen for components 20 and 24 in FIG. 3, the components are positioned to direct air over a portion of the sheet width which includes the entire cross-machine width 19 of the sensor package 15. Components 20 and 24 are secured to the upper carriage member 6, and components 22 and 26 are secured to the lower carriage member 8 as hereinafter described. Components 20 and 22 form a first pair 21 of air-directing components for guiding the sheet 2 into the housing 10. Components 24 and 26 form a second pair 25 of air-directing components for guiding the sheet 2 out from the housing 10.

Pressure-regulated air is supplied to the air-directing components 20, 22, 24, 26 from a remote source, (not shown), and conventional flow regulating means 28, 30 are provided as indicated in FIG. 5. Since air-directing components 22 and 26 must overcome the local weight of the sheet 2 to form air bearings, they can be expected to require higher flow rates than will be required for air-directing components 20 and 24. Accordingly, it is preferred that components 22 and 26 be in fluid communication with a common flow regulating means 28 while components 20 and 24 be in fluid communication with a second common flow regulating means 30.

Figure 4:
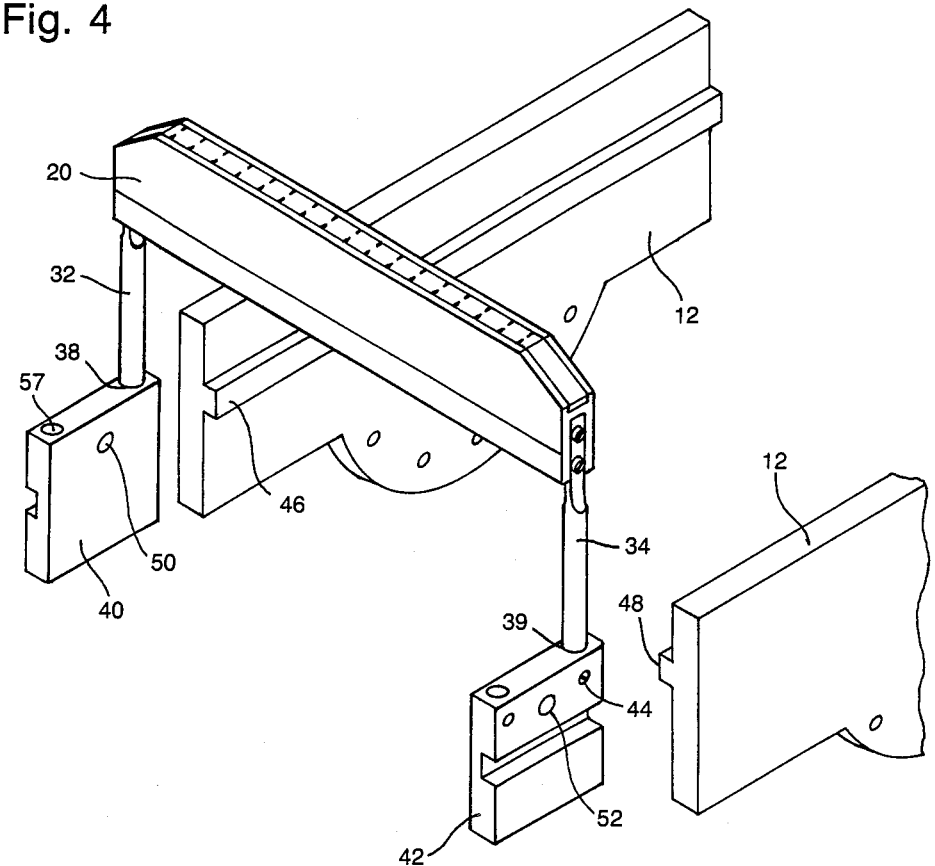
FIG. 4 is a perspective view illustrating a mounting arrangement for the air-directing components of the preferred embodiment.

As mentioned above, components 20 and 24 are secured to the upper carriage member 6, and components 22 and 26 are secured to the lower carriage member 8. This is one in the manner shown for component 20 in FIG. 4, and is similar to the manner in which the sensors 16, 17, 18 are secured to the carriage mechanism. In FIG. 4, rods 32, 34 having flattened ends are fitted and secured in slots 37 (FIG. 6) formed in each end of the component 20. The rods 32, 34 are slidably disposed within bores 38, 39 formed in slotted guide mounts 40, 42. The clearance between component 20 and its pair-counterpart (component 22) is thus adjustable by movement of the rods 32, 34 within their respective bores or by movement of similar rods for the pair-counterpart. During operation, the clearance is fixed via set-screws (as at 44). The guide mounts 40, 42 slide over square rails 46, 48 attached to interior surfaces of the upper housing 12, and are secured to the housing through threaded bores 50, 52. The upper housing 12 is bolted to the upper carriage member 6 (FIG. 1) through holes (as at 54, 56) which are arranged to provide for adjustment of the pass angle. Component 24 is secured to the opposite end of the upper carriage member 6 in similar fashion and components 22 and 26 are likewise secured to the lower carriage member 8.

The above-described mounting arrangement for the air-directing components 20, 22, 24, 26 is one of many possible arrangements, and the arrangement used is not seen as particularly important in the practice of this invention, although the feature of adjustable clearance between the components of each pair is seen as important in minimizing the air flow required to form air bearings between the sheet 2 and each component. The clearance may be positive, near zero (See, e.g. FIG. 5), or even slightly negative depending on the physical characteristics of the sheet 2.

Another important aspect of the invention is that each air-directing component may be positioned differently, as determined along the machine direction, from the air-directing component of the same pair. As shown in FIG. 4, two vertical bores (as at 38 and 57) are provided in each guide mount. Thus, any air-directing component may be inserted in either of two positions. Referring to FIG. 5, the sheet 2 travels in the machine direction indicated by the arrow 58. The first pair 21 of components is upstream from the sensor package 15 (FIG. 3), and the second pair 25 is downstream from the sensor package. The air-directing components of each pair 21, 25 are in different machine-direction positions as indicated. This difference in machine-direction positions is provided to increase sheet stability by maintaining slight tension on the sheet 2 over a range extending between the two pairs 21, 25. In addition to minimizing sheet flutter, this facilitates guiding the sheet 2 into and out from the housing 10 (FIG. 1). In operation, streams of air continuously directed from four locations corresponding to components 20, 22, 24, and 26 impinge the sheet 2 at four machine-direction positions. Components 20 and 24 direct streams of air onto a first surface 60 corresponding to the top of the sheet 2 to urge the sheet away from the components. Likewise components 22 and 26, which face generally a direction opposite that faced by their pair-counterparts, direct streams of air onto a second surface 62 corresponding to the bottom of the sheet to urge the sheet away from these components.

Arrows 64 and 66 indicate the approximate center positions of displacement ranges 68 and 70, respectively. It will be recognized from the drawing that the components of each pair 21, 25 cooperate to exert a slight rotation of the sheet 2 about positions 64 and 66, respectively. The rotation about position 64 is in a direction opposite the rotation about point 66. The two pairs 21, 25 thus cooperate to produce an increase in tension of the sheet over a range extending between the center positions 64, 66.

Figure 6:
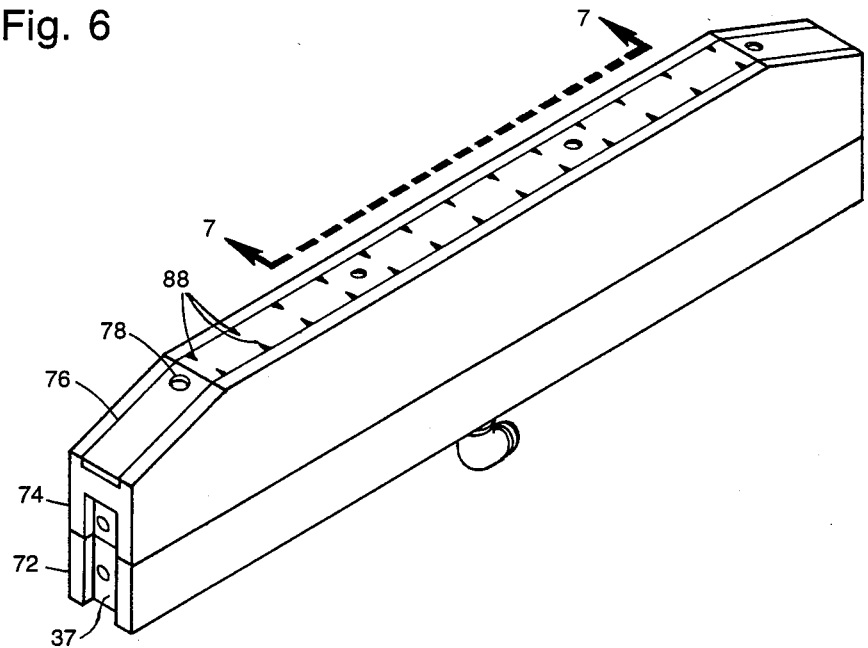
FIG. 6 is a perspective view showing the design of a suggested air-directing component for use in practicing the invention.
Figure 7:
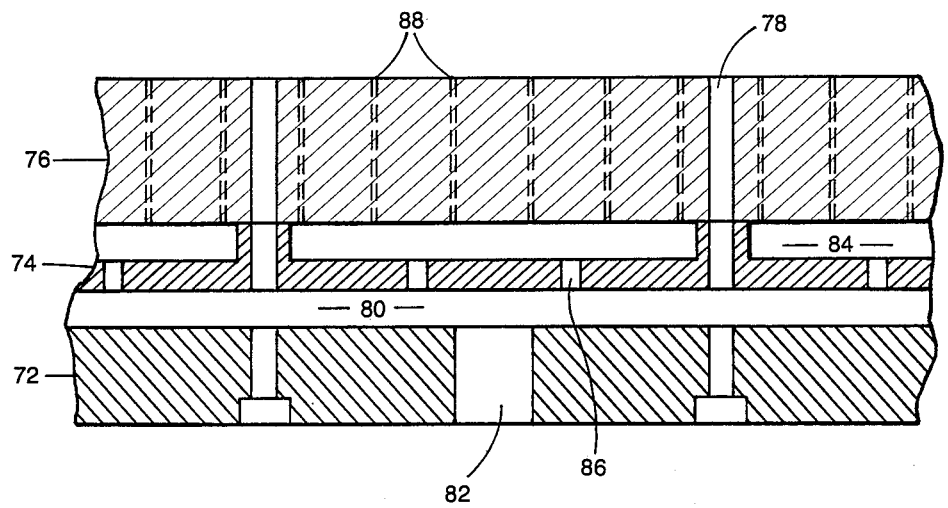
FIG. 7 is a partial, cross-sectional view of the air-directing component of FIG. 6 taken along line 7—7.

Many functionally equivalent designs for the pneumatic sheet guiding means are possible. The current design is shown in FIGS. 5 and 6 and comprises a base section 72, a staging section 74, and a delivery section 76. A channel is cut in the staging section 74 to accommodate the delivery section 76. The three sections 72, 74, 76 are secured with bolts extending through threaded bores (as at 78). An interior channel in the base section 72 is milled from the surface facing the staging section 74 to form a main plenum 80. Air flows into the main plenum 80 via a threaded supply bore 82. A plurality of separate interior channels of the staging section 74 are milled from the surface facing the delivery section 76 to form a plurality of staging plenums (as at 84). The machine-direction width of the staging plenums 84 is substantially the same as that of the delivery section 76. At least one hole (as at 86) is drilled in the staging section 74 for each staging plenum 84 to provide a flow channel between the main plenum 80 and each staging plenum. A plurality of V-notches (as at 88) are cut along hidden surfaces of the delivery section 76 to provide air delivery from the staging plenums 84 to the sheet 2. The staging plenums 84 are provided in anticipation of difficulty in maintaining air bearings when a portion of the pneumatic sheet-guiding means is "off-sheet". Thus, they are unnecessary in the case of non-scanning sensor packages, and may prove unnecessary in any event. Moreover, where the aperture or apertures (e.g. the V-notches of FIGS. 5 and 6) can be sized to provide the required air bearings at a flow rate which is near saturation, any effect from off-sheet positioning should be negligible.

Although the invention has been described in terms of the preferred embodiment, it is apparent that numerous equivalents may be resorted to without departing from the essence of the invention. For example, the invention can be used by replacing the second pair 25 of air-directing components 24, 26 with conventional guide rails, and most of the advantages provided by the invention will still be realized since guide rails positioned downstream from the sensor package 15 do not contribute as heavily to the dust buildup problem as those positioned upstream from the sensor package. In addition, it is unnecessary that the pneumatic sheet guiding means be located inside the housing 10, although such a location is preferable for both practical and aesthetic reasons. Further, it is not intended that the invention be restricted to scanning sensor packages, or to sensor packages having both upper and lower portions, and those skilled in the art will recognize that the invention can easily be adapted for other embodiments.

What is claimed is:

1. An inspection station of the type used in measuring physical properties of a continuously-moving web of paper having a direction of motion including a sensor package contained within a housing and having a cross-machine width, the sensor package being adapted to produce electrical signals indicative of one or more of the physical properties as the web is moving past the sensor package, sand sensor package including a web entrance end and a web exit end, and including sensor means on opposite sides of said web extending at least a portion of the cross-machine width, each of said sensor means including a sensor surface extending parallel to said web and spaced therefrom and wherein the improvement comprises pneumatic means to position the web in a desired path between and spaced from said sensor surfaces comprising a pair of air-directing means extending across substantially the cross-machine width of said sensor package and positioned to direct air onto opposite surfaces of said web at said web entrance end, each of said air-directing means extending out from its respective sensor surface toward said web and including at least one row of air-directing apertures for directing air onto said web surface substantially over the cross-machine width of said sensor package to space said web between said air-directing means and between and spaced from said sensor surfaces, wherein said air-directing means of said pair are spaced from each other in the direction of motion of said web.

2. An inspection station as in claim 1 and further comprising a second pair of air-directing means extending across substantially the cross-machine width of said sensor package and positioned to direct air onto opposite surfaces of said web at said web exit end, each of said air-directing means of said second pair extending out from its respective sensor surface toward said web and including at least one row of air-directing apertures for directing air onto said web surface substantially over the cross-machine width of said sensor package to space said web between said second pair of air-directing means and between and spaced from said sensor surfaces.

3. An inspection station as in claim 2 wherein said air-directing means of said second pair are spaced from each other in the direction of motion of said web.

4. An inspection station as in claim 3 wherein said air-directing means adjacent a first surface of said web at said entrance end is spaced downstream in the direction of motion of said web from said air-directing means adjacent the second surface of said web at said entrance end and wherein said air-directing means adjacent said first surface of said web at said exit end is spaced upstream in the direction of web travel from said air-directing means adjacent the second surface of said web at said exit end whereby said web is placed under tension by said air-directing means.

* * * * *